US008679814B2

(12) United States Patent
Asenjo et al.

(10) Patent No.: US 8,679,814 B2
(45) Date of Patent: Mar. 25, 2014

(54) PROTEIN AND DNA SEQUENCE ENCODING A COLD ADAPTED XYLANASE

(75) Inventors: Juan A. Asenjo, Santiago (CL);
Barbara A. Andrews, Santiago (CL);
Juan Pablo Acevedo, Santiago (CL);
Loreto Parra, Santiago (CL); Luis O. Burzio, Santiago (CL)

(73) Assignee: University of Chile, Santiago (CL)

( * ) Notice: Subject to any disclaimer, the term of this patent is extended or adjusted under 35 U.S.C. 154(b) by 69 days.

(21) Appl. No.: 13/148,227

(22) PCT Filed: Feb. 2, 2010

(86) PCT No.: PCT/EP2010/051260
§ 371 (c)(1),
(2), (4) Date: Aug. 5, 2011

(87) PCT Pub. No.: WO2010/089302
PCT Pub. Date: Aug. 12, 2010

(65) Prior Publication Data
US 2011/0287515 A1 Nov. 24, 2011

Related U.S. Application Data

(60) Provisional application No. 61/150,545, filed on Feb. 6, 2009.

(51) Int. Cl.
*C12N 9/24* (2006.01)
*C12N 1/00* (2006.01)
*C12N 1/20* (2006.01)
*C12N 15/00* (2006.01)
*C07H 21/04* (2006.01)

(52) U.S. Cl.
USPC .... 435/200; 435/69.1; 435/320.1; 435/252.3; 435/254.2; 536/23.2

(58) Field of Classification Search
None
See application file for complete search history.

(56) References Cited

U.S. PATENT DOCUMENTS

| 5,179,021 A | 1/1993 | du Manoir et al. |
| 5,223,409 A | 6/1993 | Ladner et al. |
| 5,658,765 A | 8/1997 | Noguchi et al. |
| 5,693,518 A | 12/1997 | Kofod et al. |
| 6,245,546 B1 | 6/2001 | Hansen et al. |

FOREIGN PATENT DOCUMENTS

| EP | 0507723 | 10/1992 |
| EP | 0634490 | 1/1995 |
| WO | 9203541 | 3/1992 |
| WO | 9206204 | 4/1992 |
| WO | 9217573 | 10/1992 |
| WO | 9404664 | 3/1994 |
| WO | 9517413 | 6/1995 |
| WO | 9522625 | 8/1995 |
| WO | 0218561 | 3/2002 |
| WO | 0224926 | 3/2002 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Charles C. Lee et al, "Isolation and Characterization of a Cold-Active Xylanase Enzyme from Flavobacterium sp", Current Microbiology, Springer-Verlag, NE, vol. 52, No. 2, Feb. 1, 2006, pp. 112-116, XP019365689 ISSN: 1432-0991, p. 113, paragraph 2.
Acevedo et al, "Cloning of Complete Genes for Novel Hydrolytic Enzymes from Antarctic Sea Water Bacteria by use of an Improved Genome Walking Technique", Journal of Biotechnology, Elsevier Science Publishers, Amsterdam, NL, vol. 133, No. 3, Dec. 4, 2007, pp. 227-286, XP022402118 ISSN: 0168-1656 the whole documents especially table 1 and 2.
Charles C. Lee ET al, "Cloning and Characterization of a Cold-Active Xylanase Enzyme from an Environmental DNA Library", Extremophiles: Life Under Extreme Conditions, Springer-Verlag, TOLNKD-DOI: 10-2007/s00792-005-0499-3, vol. 10, No. 4, Mar. 11, 2006.
J-C Marx et al, Cold-Adapted Enzymes from Marine Antartic Microorganisms,Marine Biotechnology, Springer-Verlag, NE, vol. 9, No. 3, Dec. 29, 2006, pp. 293-304, XP019495035, ISSN: 1436-2236, the whole document.
Collins T et al, "Xylanases, Xylanase Families and Extremophilic Xylanases", FEMS Microbiology Reviews, Elsevier, Amsterdam, NL LNKD-DOI: 10.1016/J. FEMSRE.2004.06.005,vol. 29, No. 1, Jan. 1, 2005, pp. 3-23, XP004713395, ISSN: 0168-6445, the whole document.
Kulkurni N., Shendye A., Rao M., 1999, Molecular and Biotechnological Aspects of Xylanases, FEMS Microbiology Review 23: 411-456.

(Continued)

*Primary Examiner* — Iqbal H Chowdhury
(74) *Attorney, Agent, or Firm* — Mendelsohn, Drucker & Dunleavy, P.C.

(57) ABSTRACT

A method of preparing a cold adapted xylanase by use of recombinant DNA techniques. A nucleic acid and corresponding amino acid sequences of a cold adapted xylanase, isolated from antarctic marine origin, preferably from an Antarctic bacteria (*Psychrobacter* sp.) are provided. These can be used in a variety of industrial contexts and for a variety of commercial purposes including more complete hydrolysis of lignocellulosic biomass into simple sugars that can then be fermented to products, such as liquid fuels and chemical feedstocks. The enzymes are also useful in the production methods of other industries, such as the animal feed, baking, and paper industries. Nucleic acids, corresponding amino acid sequences, constructs, expression vectors or integration vectors containing the DNA molecule, and host cells comprising the polynucleotides as well as methods for producing and using the polypeptides for producing and using the *Psychrobacter*-derived cold adapted family GH10 xylanase-like protein are also described.

9 Claims, No Drawings

(56) References Cited

OTHER PUBLICATIONS

Henrissat B., 1991, "A Classification of Glycosyl Hydrolases Based on Amino Acid Sequence Similarities", Biochem J., 280: 309-316.
Henrissat B. and Bairoch A., 1996, "Updating the Sequence of Glycosyl Hydrolases", Biochem J., 316: 695-696.
Sambrook, Fritsch and Maniatis, Second Edition, 1989, Chapter 15.
Sambrook, Fritsch and Maniatis, 2001, Molecular Cloning, a Laboratory Manual, New York: CSIL Press, Cold Spring Harbor, pp. A8.9-A8.10.
Reidhaar-Olson and Sauer, 1988, Science, 241: 53-57; Bowie and Sauer, 1989, Proc Natl Acad Sci USA, 86: 2153-2156.
Lownan et al, 1991, Biochem, 30: 10832-10887.
Derbyshire et al, 1986, Gene, 46: 145; NER et al, 1998, DNA, 7: 127.
Ness et al, 1999, "DNA Shuffling of Subgenomic Sequences of Subtilisin", Nature Biotechnology, 17: 893-896.
Protein Purification, J-C Janson and Lars Ryden, editors, VCA Publishers, New York, 1989.
G.L. Miller, 1959, "Use of Dinitrosalicylic Acid Reagent for Determination of Reducing Sugars", Anal Chem., 3: 425-428.
Juncker et al, 2003, "Prediction of Lipoprotein Signal Peptides in Gram-Negative Bacteria", Protein Sci, 12: 1652-62.

\* cited by examiner

SEQUENCE LISTING

```
<160> NUMBER OF SEQ ID NOS: 15

<210> SEQ ID NO 1
<211> LENGTH: 2223
<212> TYPE: DNA
<213> ORGANISM: Psychrobacter sp. strain 2-17

<400> SEQUENCE: 1
atgaataaat cgatttttcg taacaccgga ttagtgacct tagtgtcact tttaatggcg      60
tgcgggggga ataataaaga tacaccggtg cctgaaccca taccggaagt agtagcccct     120
gatacaccag agcctgaagc gccaatagca gctgaaataa caaatggcgg gtttgaagaa     180
gacacagcag ggcaaacaac acccgtcgga aattgggtat ttaggccaac acaagaatca     240
agcgcgactt ctactataga agtaatagaa tccgaagaag gcgttaatac ttaccaaggc     300
acaaaagcag ttgaggttaa cgttaataca ctgggtgaca acccgtgggg tattgaaata     360
gcttatgaag accttcctat caccggtggt aaaaattatg agtttagcgt ttgggccaaa     420
ggtgaagagg gaaccagtgc cgatttttgg attcaaacac ctgcgccaga ttacggtcaa     480
```

```
cttagtctag taaagaaac actcacaggc gagtggcaaa aataacatt aacagccgca      540 acggccgaag ctgactcttt agtaaggctg gcaattcact tttcaaaaga agagaacatt   600
aacaagtcta tacctaga cgaattttca ggctttattt tagacgatgt accagcacaa    660 gaaataccctg atgttcaata cagtgaagta acagcgcaaa gtttaaaagc attagcacct  720
aattttaata ttggtgtggc tgtgccagcg ggtggttttg gtaacagcgt aatagacaga   780
ccagagatta aacgattat tgaacaacac tttaatcagc tctctgctga aatattatg    840 aagcctacct atttacaacc aactcaaggt gaattttttt acgatgattc tgatgagcta   900
gttaactacg ccaaagacaa ctcactcacg gtacatggtc atgttttgt ttggcactcg    960 caaattgcgc cttggatgca aagttttcaa ggtgataaag ccgcgtggat aaccatgatg   1020
gaaaatcaca ttactcaagt ggccactcat tttgaagaag aaggcgataa cgataccgtc   1080
gttagctggg atgtagttaa cgaagcgttt atggaaaatg gtaaataccg tggtgaaaaa   1140
accactgacg acagcgccga cgaatctgta tggtttgaaa atataggagc cgaattttta   1200
ccattagcct ataaagcagc aagagcggcc gaccccgatg ccgacttata ctacaatgat   1260
tacaacctga tttggaatgc cgataaatta gatgctgtta tagctatggt taacgatttt   1320
cacaacaacg gcgtgcctat tgatggcata ggttttcaat ctcatatttc acttaacagc   1380
cctgatattt caaccattca ggcacatctt caaaaagtgg tcgatattcg ccctaaaatt   1440
aaagtaaaaa ttaccgagct agatgttcgt atgaacaacg aaggcggcat tcctctcact   1500 tacttaaacca gtgaaagagc ggatgaacaa aagcagtact actacgatat tgttaaaaca   1560
tacctagaaa ctgtacctga agatcaacgc ggtggcataa ctatttgggg cgtaattgac   1620
gaggatagct ggttgcaaaa ctggccagag ccgaaaacag aatggccgct gttatttttt   1680
aatgacttta ctgcaaagcc tgccttacaa ggatttgcta atgcattaaa agagctaatt   1740
gaagttgtac aaccagcacc ttcatcagag ctgctaacta atggcgactt tgaagccgga   1800
cttgattcct ggcaagcgcg tggcagtgca agcataaccct tagagtcaac ccaagctcat   1860
agcggtaata atagcgcttt agtacaaggg cgaactgaaa cgtggaatgg gttacaaaag   1920
gatgtaaaag gcttatttac agcagataaa acctataacg tatctgcatg ggttaagtta    1980
tctgacgata ccagtaccgt ttcaccagat ataaaactca cactacaaat agagcacact   2040
agcactgaat accttgagtt gacacctgtt acaaccgttg cagcaggtga gtgggtacag   2100
ctatcaggta cttacacaca ttcaattaca acgcaggaaa gcgccgcttt actttatgtt   2160
gagtcaagtg aactcaccgc tgacttttat gtggatgatg tatcggtaac cttggtcgaa   2220
taa                                                                 2223
```

<210> SEQ ID NO 2
<211> LENGTH: 740
<212> TYPE: PRT
<213> ORGANISM: Psychrobacter sp. strain 2-17

<400> SEQUENCE: 2

Met Asn Lys Ser Ile Phe Arg Asn Thr Gly Leu Val Thr Leu Val Ser
1               5                   10                  15

Leu Leu Met Ala Cys Gly Gly Asn Asn Lys Asp Thr Pro Val Pro Glu
            20                  25                  30

Pro Ile Pro Glu Val Val Ala Pro Asp Thr Pro Glu Pro Glu Ala Pro
        35                  40                  45

Ile Ala Ala Glu Ile Thr Asn Gly Gly Phe Glu Glu Asp Thr Ala Gly
    50                  55                  60

```
Gln Thr Thr Pro Val Gly Asn Trp Val Phe Arg Pro Thr Gln Glu Ser
 65                  70                  75                  80

Ser Ala Thr Ser Thr Ile Glu Val Ile Glu Ser Glu Gly Val Asn
             85                  90                  95

Thr Tyr Gln Gly Thr Lys Ala Val Glu Val Asn Val Asn Thr Leu Gly
                100                 105                 110

Asp Asn Pro Trp Gly Ile Glu Ile Ala Tyr Glu Asp Leu Pro Ile Thr
            115                 120                 125

Gly Gly Lys Asn Tyr Glu Phe Ser Val Trp Ala Lys Gly Glu Glu Gly
        130                 135                 140

Thr Ser Ala Asp Phe Trp Ile Gln Thr Pro Ala Pro Asp Tyr Gly Gln
145                 150                 155                 160

Leu Ser Leu Val Lys Glu Thr Leu Thr Gly Gly Trp Gln Lys Ile Thr
                165                 170                 175

Leu Thr Ala Ala Thr Ala Glu Ala Asp Ser Leu Val Arg Leu Ala Ile
            180                 185                 190

His Phe Ser Lys Glu Glu Asn Ile Asn Lys Ser Ile Tyr Leu Asp Glu
        195                 200                 205

Phe Ser Gly Phe Ile Leu Asp Asp Val Pro Ala Gln Glu Ile Pro Asp
210                 215                 220

Val Gln Tyr Ser Glu Val Thr Ala Gln Ser Leu Lys Ala Leu Ala Pro
225                 230                 235                 240

Asn Phe Asn Ile Gly Val Ala Val Pro Ala Gly Gly Phe Gly Asn Ser
                245                 250                 255

Val Ile Asp Arg Pro Glu Ile Lys Thr Ile Ile Glu Gln His Phe Asn
            260                 265                 270

Gln Leu Ser Ala Glu Asn Ile Met Lys Pro Thr Tyr Leu Gln Pro Thr
        275                 280                 285

Gln Gly Glu Phe Phe Tyr Asp Asp Ser Asp Glu Leu Val Asn Tyr Ala
290                 295                 300

Lys Asp Asn Ser Leu Thr Val His Gly His Val Phe Val Trp His Ser
305                 310                 315                 320

Gln Ile Ala Pro Trp Met Gln Ser Phe Gln Gly Asp Lys Ala Ala Trp
                325                 330                 335

Ile Thr Met Met Glu Asn His Ile Thr Gln Val Ala Thr His Phe Glu
            340                 345                 350

Glu Glu Gly Asp Asn Asp Thr Val Val Ser Trp Asp Val Val Asn Glu
        355                 360                 365

Ala Phe Met Glu Asn Gly Lys Tyr Arg Gly Glu Lys Thr Thr Asp Asp
370                 375                 380

Ser Ala Asp Glu Ser Val Trp Phe Glu Asn Ile Gly Ala Glu Phe Leu
385                 390                 395                 400

Pro Leu Ala Tyr Lys Ala Ala Arg Ala Ala Asp Pro Asp Ala Asp Leu
                405                 410                 415

Tyr Tyr Asn Asp Tyr Asn Leu Ile Trp Asn Ala Asp Lys Leu Asp Ala
            420                 425                 430

Val Ile Ala Met Val Asn Asp Phe His Asn Asn Gly Val Pro Ile Asp
        435                 440                 445

Gly Ile Gly Phe Gln Ser His Ile Ser Leu Asn Ser Pro Asp Ile Ser
        450                 455                 460

Thr Ile Gln Ala His Leu Gln Lys Val Val Asp Ile Arg Pro Lys Ile
465                 470                 475                 480

Lys Val Lys Ile Thr Glu Leu Asp Val Arg Met Asn Asn Glu Gly Gly
```

```
                    485                 490                 495
Ile Pro Leu Thr Tyr Leu Thr Ser Glu Arg Ala Asp Glu Gln Lys Gln
                500                 505                 510

Tyr Tyr Tyr Asp Ile Val Lys Thr Tyr Leu Glu Thr Val Pro Glu Asp
            515                 520                 525

Gln Arg Gly Gly Ile Thr Ile Trp Gly Val Ile Asp Glu Ser Trp
        530                 535                 540

Leu Gln Asn Trp Pro Glu Pro Lys Thr Glu Trp Pro Leu Leu Phe Phe
545                 550                 555                 560

Asn Asp Phe Thr Ala Lys Pro Ala Leu Gln Gly Phe Ala Asn Ala Leu
                565                 570                 575

Lys Glu Leu Ile Glu Val Val Gln Pro Ala Pro Ser Ser Glu Leu Leu
                580                 585                 590

Thr Asn Gly Asp Phe Glu Ala Gly Leu Asp Ser Trp Gln Ala Arg Gly
                595                 600                 605

Ser Ala Ser Ile Thr Leu Glu Ser Thr Gln Ala His Ser Gly Asn Asn
            610                 615                 620

Ser Ala Leu Val Gln Gly Arg Thr Glu Thr Trp Asn Gly Leu Gln Lys
625                 630                 635                 640

Asp Val Lys Gly Leu Phe Thr Ala Asp Lys Thr Tyr Asn Val Ser Ala
                645                 650                 655

Trp Val Lys Leu Ser Asp Asp Thr Ser Thr Val Ser Pro Asp Ile Lys
                660                 665                 670

Leu Thr Leu Gln Ile Glu His Thr Ser Thr Glu Tyr Leu Glu Leu Thr
            675                 680                 685

Pro Val Thr Thr Val Ala Ala Gly Glu Trp Val Gln Leu Ser Gly Thr
        690                 695                 700

Tyr Thr His Ser Ile Thr Thr Gln Glu Ser Ala Ala Leu Leu Tyr Val
705                 710                 715                 720

Glu Ser Ser Glu Leu Thr Ala Asp Phe Tyr Val Asp Asp Val Ser Val
                725                 730                 735

Thr Leu Val Glu
        740

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct

<400> SEQUENCE: 3 tgtttttca tggcggcgg                                                 19

<210> SEQ ID NO 4
<211> LENGTH: 17
<212> TYPE: DNA
<213> ORGANISM: Artificial Sequence
<220> FEATURE:
<223> OTHER INFORMATION: Synthetic Construct

<400> SEQUENCE: 4
ggcgatagtg ccggcgg                                                  17

<210> SEQ ID NO 5
<211> LENGTH: 447
<212> TYPE: DNA
<213> ORGANISM: Psychrobacter sp. strain 2-17
```

<400> SEQUENCE: 5

```
ggtggttttg gtaacagcgt aatagacaga ccagagatta aaacgattat tgaacaacac    60
tttaatcagc tctctgctga aaatattatg aagcctacct atttacaacc aactcaaggt   120 gaatttttt acgatgattc tgatgagcta gttaactacg ccaaagacaa ctcactcacg    180
gtacatggtc atgtttttgt ttggcactcg caaattgcgc cttggatgca aagttttcaa   240
ggtgataaag ccgcgtggat aaccatgatg gaaaatcaca ttactcaagt ggccactcat   300
tttgaagaag aaggcgataa cgataccgtc gttagctggg atgtagttaa cgaagcgttt   360
atggaaaatg gtaaataccg tggtgaaaaa accactgacg cagcgccga cgaatctgta    420 tggtttgaaa atataggagc cgaattt                                       447
```

<210> SEQ ID NO 6
<211> LENGTH: 29
<212> TYPE: DNA
<213> ORGANISM: Artificial Sequence
<220> FEATURE:
<223> OTHER INFORMATION: Synthetic Construct

<400> SEQUENCE: 6

```
ctaggccacg cgtcgactag tactagctt                                      29
```

<210> SEQ ID NO 7
<211> LENGTH: 28
<212> TYPE: DNA
<213> ORGANISM: Artificial Sequence
<220> FEATURE:
<223> OTHER INFORMATION: Synthetic Construct

<400> SEQUENCE: 7

```
agctagtact agtcgacgcg tggcctag                                       28
```

<210> SEQ ID NO 8
<211> LENGTH: 23
<212> TYPE: DNA
<213> ORGANISM: Artificial Sequence
<220> FEATURE:
<223> OTHER INFORMATION: Synthetic Construct

<400> SEQUENCE: 8

```
cacgcgtcga ctagtactag ctt                                            23
```

<210> SEQ ID NO 9
<211> LENGTH: 29
<212> TYPE: DNA
<213> ORGANISM: Artificial Sequence
<220> FEATURE:
<223> OTHER INFORMATION: Synthetic Construct

<400> SEQUENCE: 9

```
gatgcaaagt tttcaaggtg ataaagccg                                      29
```

<210> SEQ ID NO 10
<211> LENGTH: 29
<212> TYPE: DNA
<213> ORGANISM: Artificial Sequence
<220> FEATURE:
<223> OTHER INFORMATION: Synthetic Construct

<400> SEQUENCE: 10

```
ccataaacgc ttcgttaact acatcccag                                      29
```

<210> SEQ ID NO 11

```
<211> LENGTH: 29
<212> TYPE: DNA
<213> ORGANISM: Artificial Sequence
<220> FEATURE:
<223> OTHER INFORMATION: Synthetic Construct

<400> SEQUENCE: 11
ctgggatgta gttaacgaag cgtttatgg                                          29

<210> SEQ ID NO 12
<211> LENGTH: 29
<212> TYPE: DNA
<213> ORGANISM: Artificial Sequence
<220> FEATURE:
<223> OTHER INFORMATION: Synthetic Construct

<400> SEQUENCE: 12
cggctttatc accttgaaaa ctttgcatc                                          29

<210> SEQ ID NO 13
<211> LENGTH: 31
<212> TYPE: DNA
<213> ORGANISM: Artificial Sequence
<220> FEATURE:
<223> OTHER INFORMATION: Synthetic Construct

<400> SEQUENCE: 13
ctttccatgg cgtgcggggg gaataataaa g                                       31

<210> SEQ ID NO 14
<211> LENGTH: 27
<212> TYPE: DNA
<213> ORGANISM: Artificial Sequence
<220> FEATURE:
<223> OTHER INFORMATION: Synthetic Construct

<400> SEQUENCE: 14
taggctcgag ttcgaccaag gttaccg                                            27

<210> SEQ ID NO 15
<211> LENGTH: 1142
<212> TYPE: DNA
<213> ORGANISM: Psychrobacter sp. strain 2-17

<400> SEQUENCE: 15
gagaggatga tcagccacac cgggactgag acacggcccg gactcctacg ggaggcagca        60
gtggggaata ttggacaatg ggggaaaccc tgatccagcc atgccgcgtg tgtgaagaag       120
gccttttggc tgtaaagcac tttaagcagt gaagaagact ccgtggttaa tacccacgga       180
cgatgacatt agctgcagaa taagcaccgg ctaactctgt gccagcagcc gcggtaatac       240
agagggtgca agcgttaatc ggaattactg ggcgtaaagg gagcgtaggt ggctcgataa       300
gtcagatgtg aaatccccgg gctcaacctg gaactgcat ctgatactgt tgagctagag        360
tatgtgagag gaaggtagaa ttccaggtgt agcggtgaaa tgcgtagaga tctggaggaa       420
taccgatggc gaaggcagcc ttctggcata atactgacac tgaggctcga aagcgtgggt       480
agcaaacagg attagatacc ctggtagtcc acgccgtaaa cgatgtctac tagtcgttgg       540
gtcccttgag gacttagtga cgcagctaac gcaataagta gaccgcctgg ggagtacggc       600
cgcaaggtta aaactcaaat gaattgacgg gggcccgcac aagcggtgga gcatgtggtt       660
taattcgatg caacgcgaag aaccttacct ggtcttgaca tatctagaat cctgcagaga       720
tgcgggagtg ccttcgggaa ttagaataca ggtgctgcat ggctgtcgtc agctcgtgtc       780
```

-continued

```
gtgagatgtt gggttaagtc ccgcaacgag cgcaaccctt gtccttagtt accagcgggt        840
taagccgggg actctaagga tactgccagt gacaaactgg aggaaggcgg ggacgacgtc        900
aagtcatcat ggcccttacg accagggcta cacacgtgct acaatggtag gtacagaggg        960
cagctacaca gcgatgtgat gcgaatctca aaaagcctat cgtagtccag attggagtct       1020
gcaactcgac tccatgaagt aggaatcgct agtaatcgcg gaatcactag tgaattcgcg       1080
gccgcctgca ggtcgaccat atgggagagc tcccaacgcg ttggatgcat agcttgagta       1140
tt                                                                     1142
```

PROTEIN AND DNA SEQUENCE ENCODING A COLD ADAPTED XYLANASE

BACKGROUND OF THE INVENTION

1. Field of the Invention

The present invention relates to purified nucleic acids encoding Antarctic bacteria (*Psychrobacter* sp.) derived enzymes such as xylanases, which can be a protein, and to purified polypeptides that have high activity and belong to the Family GH10 xylanase-like enzymes. The present invention also provides a genetically recombinant xylanase, with high xylanase activity and having cold adapted activity. The present invention also relates to a process for the production of the recombinant xylanase. The invention also relates to nucleic acids, the corresponding amino acid sequences, constructs, expression vectors or integration vectors containing the DNA molecule, and host cells comprising the polynucleotides as well as methods for producing and using the polypeptides. Furthermore, the present invention relates to a method of preparing the cold adapted xylanase by use of recombinant DNA techniques.

2. Description of the Prior Art

Xylans are heteropolysaccharides which form the major part of the hemicellulose present in the plant biomass. Xylan is a polymer of D-xylose linked by β-1,4-xylosidic bonds. Many different side groups could bind to these residues like acetyl, arabinosyl and glucuronosyl residues. Xylan can be degraded to xylose and xylo-oligomers by acid or enzymatic hydrolysis. Enzymatic hydrolysis of xylan produces free sugars without the by-products formed with acid (e.g. furans).

Endoxylanases hydrolyze specifically the backbone of the hemicellulose. In some cases, the side groups may mask the main chain by steric hindrance. Different xylanase activities already described are characterized by their specificity towards their substrate and the length of the oligomers produced.

Enzymes capable of degrading xylan and other plant cell wall polysaccharides are important in various industrial areas. Xylanases are used in the pulp, paper, feed and bakery industries. Other applications include the juice and beer industries, where their ability to catalyse the degradation of the backbone or sidechains of the plant cell wall polysaccharide is utilized. Xylanases could also be used in the wheat separation process. The observed technological effects are, among others, improved bleachability of the pulp, decreased viscosity of the feed or changes in dough characteristics. Others applications for xylanases are enzymatic breakdown of agricultural wastes for production of alcohol fuels, enzymatic treatment of animal feeds for hydrolysis of pentosans and manufacturing of dissolving pulps yielding cellulose.

Xylanases, e.g., endo-β-1,4-xylanase (EC 3.2.1.8), which hydrolyze the xylan backbone chain, have been studied for their use in bleaching lignocellulosic material. For example, in U.S. Pat. No. 5,179,021, the combination of xylanase and oxygen treatment in the bleaching of pulp is disclosed as being particularly useful. WO 92/17573 discloses a substantially pure xylanase derived from *Humicola insolens* and recombinant DNA encoding said xylanase for use as a baking agent, a feed additive, and in the preparation of paper and pulp. In PCT Application Publication No. WO 92/03541, a method of dissolving hemicellulose with hemicellulases derived from the fungus *Trichoderma reesei* is disclosed.

There is great interest in discovering different xylanases that will function at the various reaction conditions used in industry for different applications. Much of the research has been directed at discovering thermoactive enzymes. By elevating the temperature, the rates of the reaction are increased. The higher reaction temperatures are appealing for reasons such as sterilization, enhanced reaction rate, and increased availability of substrate, but there is decreased process-energy efficiency. There has been much less work on cold-active xylanases. However, this class of enzymes has received increasing interest because some industrial processes require the use of lower temperatures to avoid altering or denaturing the product. There can also be considerable energy savings for those reactions that can be efficiently conducted at lower temperatures (Kulkurni N, Shendye A, Rao M. 1999. Molecular and biotechnological aspects of xylanases, FEMS Microbiology Review 23: 411-456).

It is an object of the present invention to provide new polypeptides having xylanase activity and nucleic acids encoding the polypeptides.

SUMMARY OF THE INVENTION

In one aspect, the present invention relates to a novel protein with cold-adapted xylanase activity and the coding nucleic acid sequence, which can be isolated from a bacterial strain of *Psychrobacter* sp.

In another aspect, the present invention relates to methods for the production of a protein with xylanase activity.

A still further aspect of the present invention relates to novel recombinant vectors containing the DNA molecule and host cells transformed therewith according to the process of the present invention.

One embodiment of the present invention is a substantially pure nucleic acid comprising a nucleic acid encoding a polypeptide having at least about 80% homology (such as identity) to a *Psychrobacter*-derived cold adapted family GH10 xylanase-like protein or a reference protein, such as the polypeptide of SEQ ID NO: 2, and more preferably, at least about 90% homology, and even more preferably, at least about 95% homology. The level of homology (such as identity) applies to all embodiments of the invention.

In certain embodiments, the substantially pure nucleic acid comprises an engineered nucleic acid variant encoding a polypeptide differing from a reference protein (SEQ ID NO: 2) or a *Psychrobacter*-derived cold adapted family GH10 xylanase-like protein by no more than about 30 amino acid substitutions, and more preferably, no more than about 20 amino acid substitutions. Preferably, the engineered substitutions cause a conservative substitution in the amino acid sequence of a reference sequence or a cold adapted protein. The invention additionally relates to vectors capable of reproducing in a cell, such as a eukaryotic or prokaryotic cell, a nucleic acid identical to sequence of SEQ ID NO: 1 as well as transformed cells having such a nucleic acid. Another embodiment of the invention is a transformed cell, such as a prokaryotic or eukaryotic cell, comprising a nucleic acid encoding a polypeptide having at least about 80% homology to a reference sequence or *Psychrobacter*-derived cold adapted family GH10 xylanase-like protein. Preferably, the transformed cell expresses one of the enzymes described herein. Yet another embodiment of the invention is a vector capable of reproducing in a cell such as a eukaryotic or prokaryotic cell. The vector comprises a nucleic acid encoding a polypeptide having at least about 80% homology to a reference sequence or *Psychrobacter*-derived cold adapted family GH10 xylanase-like protein SEQ ID NO: 2. Preferably, the vector of the invention codes for expression, either intracellularly or extracellularly, of the cold adapted xylanase-like protein described herein.

Another embodiment of the present invention is a polypeptide comprising a substantially pure isoform of a reference sequence or a *Psychrobacter*-derived cold adapted family GH10 xylanase-like protein or engineered variant thereof, and preferably, a polypeptide comprising SEQ ID NO: 2.

In another aspect, the present invention also relates to methods of using the polypeptides in treating pulp, in processes for producing xylose or xylo-oligosaccharide, as feed enhancing enzymes that improve feed digestibility, in baking, and in brewing.

Yet another embodiment of the invention is a method of preparing an enzyme such as a xylanase-like enzyme, wherein the protein has at least about 80% homology to a reference sequence or a *Psychrobacter*-derived multifunctional protein. Such method may comprise the steps of:

1. Constructing a recombinant chimeric expression vector, comprising a nucleic acid sequence of the present invention such as SEQ ID NO: 1.
2. Transforming an appropriate eukaryotic or prokaryotic host cell with the expression vector for expressing, either intracellularly or extracellularly, a nucleic acid encoding the protein; and
3. Growing the transformed cell in culture and isolating the protein from the transformed cell or the culture medium.

These aspects of the invention, together with other objects and advantages which will become subsequently apparent reside in the detailed construction and operation as more fully hereinafter described and claimed.

DETAILED DESCRIPTION OF EMBODIMENTS
OF THE INVENTION

Although only certain embodiments of the invention are explained in detail, it is to be understood that the invention is not limited in its scope to the details set forth in the following description. The invention is capable of other embodiments and of being practiced or carried out in various ways. Also, in describing these embodiments, specific terminology will be resorted to for the sake of clarity. It is to be understood that each specific term includes all technical equivalents which operate in a similar manner to accomplish a similar purpose.

Definitions

"Iso form" refers to a naturally occurring sequence variant of a substantially homologous protein within the same organism. Preferably, the iso form shares at least about 85% identity, and more preferably, at least about 90% identity with one of the following sequences of amino acid residues:

amino acid residues 21-740 of SEQ ID NO: 2.
amino acid residues 21-576 of SEQ ID NO: 2.
amino acid residues 53-576 of SEQ ID NO: 2.
amino acid residues 53-740 of SEQ ID NO: 2.
amino acid residues 234-576 of SEQ ID NO: 2.
amino acid residues 234-740 of SEQ ID NO: 2.

"Xylanase activity": the term "xylanase" is defined herein as 1,4-β-D-xylan-xylanohydrolase (E.C. 3.2.1.8) which catalyzes the endohydrolysis of 1,4-β-D-xylosidic linkages in xylans. For purposes of the present invention, xylanase activity is determined with birchwood xylan as the substrate in 50 mM Tris/HCl, 2 mM $CaCl_2$, pH 8.0 buffer at 20° C.

"Family GH10 xylanase" is defined herein as a polypeptide falling into the glycoside hydrolase Family 10 according to Henrissat B., 1991, "A classification of glycosyl hydrolases based on amino acid sequence similarities" *Biochem. J.,* 280: 309-316, and Henrissat B. and Bairoch A., 1996, "Updating the sequence-based classification of glycosyl hydrolases," *Biochem. J.,* 316: 695-696.

"*Psychrobacter*-derived cold adapted family GH10 xylanase-like protein" refers to a cold adapted xylanase-like protein having the same sequence as a protein isolated from *Psychrobacter* sp. strain 2-17 and having the properties of the protein described in the section entitled "Preferred Characteristics of the Cold Adapted xylanase-like Protein" of this patent. The amino acid sequence included in SEQ ID NO: 2 or other isoforms thereof or chimeric polypeptides thereof are examples of *Psychrobacter*-derived cold adapted family GH10 xylanase-like protein.

"Percent sequence identity" refers to the percentage of two sequences that are deemed identical or homologous within the skill of the art. To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). Alignment for purposes of determining percent amino acid sequence identity can be achieved in various ways that are within the skill of the art, for example, using publicly available computer software such as BLAST-2 software that are set to their default parameters. Those skilled in the art can determine appropriate parameters for measuring alignment, including any algorithms needed to achieve maximal alignment over the full length of the sequences being compared. The ClustalW (1.60) alignment method is used in this application.

"Genome walking method" refers to a technique for isolating polynucleotides of unknown sequence regions on either side of known ones; they are collectively known as genome walking or chromosome walking techniques.

"Polynucleotide" refers to a polymer of DNA or RNA which can be single- or double-stranded, optionally containing synthetic, non-natural or altered nucleotide bases capable of incorporation into DNA or RNA polymers. The polynucleotide may be in the form of a separate fragment or as a component of a larger nucleotide sequence construct.

"Expression" includes any step involved in the production of the polypeptide including, but not limited to, transcription and secretion.

"Expression vector" refers herein to a linear or circular DNA molecule that comprises a polynucleotide encoding a polypeptide of the invention, and which is operably linked to additional nucleotides that allow its expression.

"Host cell", includes any cell type which is susceptible to transformation, transfection, transduction, and the like with a nucleic acid construct or expression vector comprising a polynucleotide of the present invention.

"Modification" means herein any chemical modification of the SEQ ID NO: 2, as well as genetic manipulation of the DNA encoding that polypeptide. The modifications can be substitutions, deletions and/or insertions of one or more amino acids as well as replacement of one or more amino acid side chains.

DETAILED DESCRIPTION OF EMBODIMENTS
THE INVENTION

Partial sequences encoding for a protein from a specific family can be isolated by polymerase chain reaction (PCR) with primers designed from consensus sequences. Several methods have been described for the isolation of unknown regions on either side of the partially sequenced ones; they are collectively known as genome walking or chromosome walking techniques. Genome walking techniques based on PCR are more successful as they are fast and less labor intensive (Acevedo et al., 2008, "Cloning of complete genes for novel hydrolytic enzymes from Antarctic sea water bacteria by use of an improved genome walking technique," *J. Biotechnol.*, 133, 277-86).

In an embodiment of the present invention, a wildtype partial sequence of a xylanase gene is preferably obtained by PCR amplification with the primers (SEQ ID NOS: 3, 4) from a *Psychrobacter* sp. strain 2-17 which was isolated from seawater collected at Frei Montalva Base (Lat 62° 11"S Long 58° 58"W), King George Island, Chilean Antarctic. This strain was characterized by the nucleic acid sequence of its 16S rRNA gene which is identical to the sequence of SEQ ID NO: 15.

The resulting gene fragment is preferably used to complete the rest of the *Psychrobacter*-derived cold adapted family GH10 xylanase-like protein implementing a new method of genome walking (Acevedo et al., 2008, "Cloning of complete genes for novel hydrolytic enzymes from Antarctic sea water bacteria by use of an improved genome walking technique," *J. Biotechnol.*, 133, 277-86).

Polynucleotides and Polypeptides Having Xylanase Activity

The polynucleotide embodiments of the invention are preferably deoxyribonucleic acids (DNAs), both single- and double-stranded, and most preferably double-stranded DNAs. However, they can also be, without limitation, ribonucleic acids (RNAs), as well as hybrid RNA:DNA double-stranded molecules.

The present invention encompasses polynucleotides encoding a *Psychrobacter*-derived cold adapted family GH10 xylanase-like protein, whether native or synthetic, RNA, DNA, or cDNA, that encode the protein, or the complementary strand thereof, including, but not limited to, nucleic acids found in a cold adapted xylanase protein-expressing organism. For recombinant expression purposes, codon usage preferences for the organism in which such a nucleic acid is to be expressed are advantageously considered in designing a synthetic cold adapted xylanase protein-encoding nucleic acid.

The nucleic acid sequences can be further mutated, for example, to incorporate useful restriction sites. See Sambrook et al., "Molecular Cloning, a Laboratory Manual," (Cold Spring Harbor Press, 1989). Such restriction sites can be used to create "cassettes", or regions of a nucleic acid sequence that are easily substituted using restriction enzymes and ligation reactions. The cassettes can be used, for example, to substitute synthetic sequences encoding mutated cold adapted xylanase-like protein amino acid sequences.

The nucleic acid sequences of the present invention can encode, for example, one of several iso forms of a *Psychrobacter*-derived family GH10 xylanase-like protein, cold adapted or artificial variants of this modified by several mutations which provide new properties such as thermo-stabilized variants.

This *Psychrobacter*-derived cold adapted family GH10 xylanase-like gene is operably linked to a nucleotide sequence encoding a signal peptide consisting of nucleotides 1 to 60 of SEQ ID NO: 1. The signal sequence is the segment of the protein that is present in the precursor protein in the bacterial cell but absent in the protein after secretion to the extracellular environment. The signal sequence corresponds to amino acid residues 1-20 in SEQ ID NO: 2: "Met Asn Lys Ser Ile Phe Arg Asn Thr Gly Leu Val Thr Leu Val Ser Leu Leu Met Ala." The remaining amino acid sequences of the polypeptides represent the protein.

Various embodiments of the *Psychrobacter*-derived cold adapted family GH10 xylanase-like protein, include, but are not limited to, an amino acid sequence as shown in SEQ ID NO: 2; as well as positions 20-740 of SEQ ID NO: 2, positions 53-576 of SEQ ID NO: 2, positions 53-740 of SEQ ID NO: 2, positions 234-740 of SEQ ID NO: 2 and positions 234-576 of SEQ ID NO: 2, which could be individually active. Additional embodiments of the *Psychrobacter*-derived cold adapted family GH10 xylanase-like protein comprise amino acid sequences which form part of the catalytic site of SEQ ID NO: 2, i.e. positions 358-378 and 476-496 of SEQ ID NO: 2. Stated another way, such embodiments comprise nucleotide sequences 1072-1134 and 1426-1488 of SEQ ID NO: 1. Other embodiments of the *Psychrobacter*-derived cold adapted family GH10 xylanase-like protein comprise amino acid sequences which are recognized as the carbohydrate binding domain in SEQ ID NO: 2, i.e. positions 53-210 and 589-740 of SEQ ID NO: 2. Such embodiments comprise nucleotide sequences 157-630 and 1775-2223 of SEQ ID NO: 1 respectively. Other embodiments of the *Psychrobacter*-derived cold adapted family GH10 xylanase-like protein comprise amino acid sequences which are recognized as the catalytic domain of Glycosyl hydrolase family 10 in SEQ ID NO: 2, i.e. positions 234-576 of SEQ ID NO: 2. Such embodiments comprise nucleotide sequence 700-1728 of SEQ ID NO: 1.

Preferably, the nucleic acids will encode polypeptides having at least about 80% homology, more preferably, at least about 90% homology, even more preferably, at least about 95% homology to a reference protein or a *Psychrobacter*-derived cold adapted family GH10 xylanase-like protein, such as the polypeptides of SEQ ID NO: 2 or other naturally occurring isoforms.

The processed protein of the polypeptide of SEQ ID NO: 2 is about 44% identical to the endo-β-1,4 xylanase from *Cellvibrio mixtus* according to the sequence provided by Genbank (Mountain View, Calif.), database acquisition no. CAA88762, and about 41% identical to endo-β-1,4 xylanase from *Cellvibrio japonicus*, according to the sequence provided by Genbank, database acquisition no. CAA88764. Preferably, the nucleic acids encoding polypeptides having cold adapted xylanase activity are less than about 80% identical to the above-identified xylanases of *Cellvibrio mixtus* or *Cellvibrio japonicus*.

The cold adapted xylanase-like protein-encoding sequence can be, for instance, substantially or fully synthetic. For recombinant expression purposes, codon usage preferences for the organism in which such a nucleic acid is to be expressed are advantageously considered in designing a synthetic cold adapted protein-encoding nucleic acid. Since the nucleic acid code is degenerate, numerous nucleic acid sequences can be used to create the same amino acid sequence. This natural "degeneracy" or "redundancy" of the genetic code is well known in the art. It will thus be appreciated that the nucleic acid sequence shown in the Sequence Listing provides only an example within a large but definite group of nucleic acid sequences that will encode the relevant polypeptides as described herein.

Polypeptides of the present invention preferably include all polypeptides encoded by the nucleic acids having the sequence identical to SEQ ID NO: 1 or its degenerate variants thereof, and all polypeptides comprising the amino acid sequences shown as:
  a) amino acid residues 21-740 of SEQ ID NO: 2,
  b) amino acid residues 21-576 of SEQ ID NO: 2,
  c) amino acid residues 53-576 of SEQ ID NO: 2,
  d) amino acid residues 53-740 of SEQ ID NO: 2,
  e) amino acid residues 234-576 of SEQ ID NO: 2, and
  f) amino acid residues 234-740 of SEQ ID NO: 2,
as well as all obvious variants of these peptides that can be made and used by a person skilled in the art. In addition, the polypeptides according to the present invention have, preferably at least about 80% sequence identity, also preferably at least about 90% sequence identity, more preferably at least 95% sequence identity, also more preferably at least 96% sequence identity, even preferably at least 97% sequence identity, even more preferably at least about 98% sequence identity, still preferably at least 99% sequence identity to an amino acid sequence selected from:
 a) amino acid residues 21-740 of SEQ ID NO: 2,
 b) amino acid residues 21-576 of SEQ ID NO: 2,
 c) amino acid residues 53-576 of SEQ ID NO: 2,
 d) amino acid residues 53-740 of SEQ ID NO: 2,
 e) amino acid residues 234-576 of SEQ ID NO: 2, and
 f) amino acid residues 234-740 of SEQ ID NO: 2.

A modified sequence derived from the DNA molecule is understood to mean any DNA molecule obtained by modification of one or more nucleotides of the gene which codes for the xylanase of the invention. The techniques for obtaining such sequences are known to a person skilled in the art, and are described, in particular, in "Molecular Cloning-a laboratory manual," Sambrook, Fritsch and Maniatis, Second Edition, 1989, Chapter 15. Usually, the modified sequence derived from the DNA molecule comprises at least about 80% homology of the calculated amino acid sequence with the sequence of SEQ ID NO: 2. As a special preference, the modified sequence derived from the DNA molecule comprises at least about 90% homology of the calculated amino acid sequence with the sequence of SEQ ID NO: 2.

Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylpro line.

Alternatively, the amino acid changes are of such a nature that the physico-chemical properties of the polypeptides are altered. For example, amino acid changes may improve the thermal stability of the polypeptide, alter the substrate specificity, change the optimum pH for the polypeptide, and the like. Essential amino acids in the parent polypeptide can be identified according to procedures known in the art, such as site-directed mutagenesis. Single or multiple amino acid substitutions can be made and tested using known methods of mutagenesis, recombination, and/or shuffling, followed by a relevant screening procedure, such as those disclosed by Reidhaar-Olson and Sauer, 1988, Science, 241: 53-57; Bowie and Sauer, 1989, Proc. Natl. Acad. Sci. USA, 86: 2152-2156; WO 95/17413 and WO 95/22625. Other methods that can be used include error-prone PCR, phage display (e.g., Lowman et al., 1991, Biochem, 30: 10832-10837; U.S. Pat. No. 5,223, 409 and WO 92/06204), and region-directed mutagenesis (Derbyshire et al., 1986, Gene, 46: 145; Ner et al., 1988, DNA, 7: 127).

Mutagenesis/shuffling methods can be combined with high-throughput, automated screening methods to detect activity of cloned, mutagenized polypeptides expressed by host cells (Ness et al., 1999, "DNA Shuffling of subgenomic sequences of subtilisin," Nature Biotechnology, 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

Methods of Synthesizing Polypeptides
 1. Expression Vectors

The present invention also relates to recombinant expression vectors comprising a nucleic acid sequence of the present invention, a promoter, and transcriptional and translational stop signals. The nucleic acid sequence of the present invention may be expressed by inserting the nucleic acid sequence or a nucleic acid construct comprising the sequence as identified in SEQ ID NO: 1 or its degenerate variants thereof, into an appropriate vector for expression, comprising the nucleotide sequences shown as:
 a) positions 61-2220 of SEQ ID NO: 1,
 b) positions 61-1728 of SEQ ID NO: 1,
 c) positions 157-1728 of SEQ ID NO: 1,
 d) positions 157-2220 of SEQ ID NO: 1,
 e) positions 700-1728 of SEQ ID NO: 1, and
 f) positions 700-2220 of SEQ ID NO: 1.

In creating the expression vector, the coding sequence is located in the vector so that it is operably linked with the appropriate control sequences for expression.

The recombinant expression vector may be any vector (e.g., a plasmid) which can be conveniently subjected to recombinant DNA procedures and can bring about the expression of the nucleic acid sequence. The choice of the vector will typically depend on the compatibility of the vector with the host cell into which the vector is introduced. The vectors may be linear or closed circular plasmids.

The vector may be an autonomously replicating vector, i.e., a vector which exists as an extra chromosomal entity and its replication is independent of chromosomal replication, e.g., a plasmid, an extra chromosomal element, a mini-chromosome, or an artificial chromosome. The vector may contain any means for assuring self-replication. Alternatively, the vector may be one which, when introduced into the host cell, is integrated into the host cell's genome and replicated together with the chromosome(s). Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene whose expression product provides for biocidal or viral resistance, resistance to heavy metals, prototrophy to auxotrophs, and the like. Examples of bacterial selectable markers are those which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. The amdS and pyrG genes of *Aspergillus nidulans* or *Aspergillus oryzae* and the bar gene of *Streptomyces hygroscopicus* are preferred for use in *Aspergillus* cells.

The vectors of the present invention preferably contain an element that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or non-homologous recombination. Alternatively, the vector may contain additional nucleic acid sequences for directing integration by homologous recombination into the genome of the host cell. The additional nucleic acid sequences enable the vector to be integrated into the host cell genome at one or more precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. Alternatively, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAM.beta.1 permitting replication in *Bacillus*. Examples of origins of replication for use in a yeast host cell are the 2 micron origin of replication, ARS1, ARS4, the combination of ARS1 and CEN3, and the combination of ARS4 and CEN6.

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected by cultivating the cells in the presence of an appropriate selectable agent.

The procedures used to ligate the elements described above to construct the recombinant expression vectors of the present invention are well known to one skilled in the art (see, e.g., Sambrook et al., 1989, supra).

2. Host Cells

The present invention also relates to recombinant host cells, comprising a nucleic acid sequence of the present invention for the recombinant production of the polypeptides. A vector comprising a nucleic acid sequence of the present invention is introduced into a host cell so that the vector is maintained as a chromosomal integrant or as a self-replicating extra-chromosomal vector as described earlier. The choice of a host cell will, to a large extent, depend upon the gene encoding the polypeptide and its source.

The host cell may be a unicellular microorganism, e.g., a prokaryote and unicellular eukaryote (yeast), or a non-unicellular organism, e.g., a eukaryote. The host cell may be a prokaryotic, such as a bacterial cell. "Bacteria" as used herein includes the gram-negative bacteria *Escherichia coli*.

Useful unicellular cells are bacterial cells such as gram-positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* or *Streptomyces murinus*, or gram-negative bacteria such as *E. coli* and *Pseudomonas* sp.

The introduction of a vector into the host cell may, for instance, be achieved by cell transformation through electroporation or conjugation, using competent cells.

3. Production

The present invention also relates to a method for producing a polypeptide of the invention, the method comprising (a) cultivating a recombinant host cell as described above under conditions conducive to the production of the polypeptide, and (b) recovering the polypeptide from the cells and/or the culture medium.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions. If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989). The polypeptides of the present invention may need additional purification. Techniques are applied as needed, including without limitation, FPLC (Pharmacia, Uppsala, Sweden) and HPLC (e.g., using gel filtration, reverse-phase or mildly hydrophobic columns).

Preferred Characteristics of Cold Adapted Xylanase

Antarctic Bacteria, including without limitation Bacteria of the genus *Psychrobacter*, is the preferred source of *Psychrobacter*-derived cold adapted family GH10 xylanase-like protein.

Preferably, the protein has a molecular weight between about 36 kd and about 170 kd, and more preferably from about 39 kd to about 91 kd, and most preferably about 82 kd, as determined by sodium dodecyl sulfate ("SDS") polyacrylamide gel electrophoresis ("PAGE"). Further, the protein preferably has substantial homology to a *Psychrobacter*-derived cold adapted family GH10 xylanase-like protein.

Xylanase activity can be preferably determined by the method of DNS. The DNS method consists of the incubation of the enzyme sample with the substrate at a required temperature and time. The reaction is stopped adding DNS reactive in a 1:1 volumetric proportion with the substrate-enzyme reaction. For each 100 ml of DNS reactive 1 g of dinitrosalicylic acid, 20 ml of NaOH 2N and 30 g of potassium and sodium tartrate (Rochelle salt) were added. Enzymatic reaction is finished by boiling the samples for 10 minutes and then cooling them in ice for 5 minutes. The enzyme activity is analyzed for total reducing sugars measuring the absorbance at 550 nm (G. L. Miller, 1959, "Use of dinitrosalicylic acid reagent for determination of reducing sugars," *Anal. Chem.*, 3, 426-428).

For the substrate birchwood xylan, the pH optimum of the cold adapted protein is preferably from about 5 to about 12, more preferably, from about 5 to about 9, and more preferably, from about 6 to about 8.

Preferably, the cold adapted xylanase-like protein of the invention has a temperature optimum for activity against birchwood xylan in the range of about 35° C. to about 40° C. The cold adapted subtilisin-like protein still shows high activity at lower temperatures (e.g. 4-20° C.).

Enhanced Xylanase Activity

The invention also relates to a modified xylanase, that is to say an enzyme whose amino acid sequence differs from that of the wild-type enzyme by at least one amino acid. Modification of the nucleotide sequence may be performed by subjecting the parent cell to mutagenesis and selecting for mutant cells with enhanced activity. The mutagenesis, which may be specific or random, may be performed, for example, by use of a suitable physical or chemical mutagenizing agent such as exposure to ultraviolet radiation or to chemical products such as ethyl methanesulphonate (EMS), N-methyl-N-nitro-N-nitrosoguanidine (MNNG), sodium nitrite or O-methyl-hydroxylamine, or by genetic engineering techniques such as, for example, site-directed mutagenesis or random mutagenesis. Furthermore, the mutagenesis may be performed by use of any combination of these mutagenizing agents. These techniques are known to a person skilled in the art and are described, in particular, in, "Molecular Cloning, a laboratory manual," Sambrook, Fritsch, Maniatis, second edition, 1989, Chapter 15.

Uses

The present invention also relates to enzyme compositions comprising the xylanase according to the invention and at least one additive. These additives are known to a person skilled in the art and are chosen according to the use envisaged for the composition. They must be compatible with the xylanase and must have little or no effect on the enzyme activity of the xylanase. Usually, these additives are enzyme stabilizers, preservatives and formulation agents.

The enzyme compositions comprising the xylanase of the present invention may be used in solid or liquid form.

The enzyme compositions may be formulated according to the anticipated use. Stabilizers or preservatives may also be added to the enzyme compositions comprising the xylanase according to the invention. For example, it is possible to stabilize the xylanase by adding propylene glycol, ethylene glycol, glycerol, starch, xylan, a sugar such as glucose and sorbitol, a salt such as sodium chloride, calcium chloride, potassium sorbate and sodium benzoate or a mixture of two or more of these products. Good results have been obtained with propylene glycol. Good results have also been obtained with sorbitol.

The xylanase and xylanase-containing compositions according to the invention may be provided to numerous outlets in various industries such as, for example, the food industry, pharmaceutical industry, bio fuel industry, paper industry or the chemical industry.

The xylanase and xylanase-containing compositions may be used, in particular, in a bakery. An example of use of a xylanase in bakery is described, in particular, in International Patent Application WO 94/04664, the disclosure of which use is hereby incorporated by reference.

The xylanase can also be used, in particular, for the treatment of paper pulp. An example of the use of a xylanase for the treatment of paper pulp is described, in particular, in European Patent Application no. 0 634 490 and U.S. Pat. No. 5,658,765, the disclosures of which uses are hereby incorporated by reference.

The polypeptides may also be used in processes for producing xylose or xylo-oligosaccharide according to, for example, U.S. Pat. No. 5,658,765, the disclosure of which use is hereby incorporated by reference.

The xylanase can also be used, in particular, in animal feeds. An example of the use of xylanase as a feed enhancing enzyme that improve feed digestibility to increase the efficiency of its utilization is described, in particular, in European Patent Application no. 0 507 723 and U.S. Pat. No. 6,245,546, the disclosure of which use is hereby incorporated by reference.

A polypeptide having xylanase activity of the present invention may be used in several applications to degrade or convert a xylan-containing material by treating the material with an effective amount of the polypeptide (see, for example, WO 2002/18561, the disclosure of which use is hereby incorporated by reference).

The polypeptides may also be used in baking according to, for example, U.S. Pat. No. 5,693,518, the disclosure of which use is hereby incorporated by reference.

The polypeptides may further be used in brewing according to, for example, WO 2002/24926, the disclosure of which use is hereby incorporated by reference.

EXAMPLES

Materials

Materials and/or chemicals used as buffers and substrates were commercial products of at least reagent grade.

Strains

In January 2003, seawater was collected from the Frei Montalva Base (Lat 62° 11"S Long 58° 58"W) at King George Island, Chilean Antarctic. Psychrotrophic bacteria were isolated on agar plates of marine medium 2216 (Difco) incubated at 4° C. The strains isolated from Antarctic seawater were grown in nutrient marine medium 2216 (Difco manual) at 4° C. and maintained on plates of marine agar 2216 at the same temperature.

*Escherichia coli* strain DH5α (F-Φ80dlacΔM15 Δ(lacayaargF)U169 recA1 endA1 hsdR178rk−, mk+) phoA supE44λ- thi-1 gyrA96 relA1), was used as the recipient strain for plasmids with gene encoding or partial encoding recombinant xylanase protein and was obtained from Invitrogen (CA-USA) and grown in LB medium at 37° C.

*Escherichia coli* strain BL21 (F-ompT hsdSB (rB-mB+) gal dcm (DE3)), was used for expression of the xylanase genes encoding recombinant protein and was obtained from Invitrogen (CA-USA) and grown in TB medium at 37° C.

Media

LB medium was composed per liter of 10 g of triptone, 5 g of yeast extract and 5 g of NaCl.

TB medium was composed per liter of 12 g of triptone, 24 g of yeast extract, 4 mL glycerol, 2.3 g of $KH_2PO_4$ and 12.5 g of $K_2HPO_4$ The present invention is further exemplified by the following non-limiting examples.

Example 1

DNA Cloning of Characterized Protein of the Invention

Nucleic Acid Manipulation

DNA manipulation was carried out as described in Sambrook et al., "Molecular Cloning, a Laboratory Manual," (Cold Spring Harbor Press, 1989). PCR products were purified from agarose gel after electrophoresis by QIAEXII supplied by QIAGEN Inc. (CA, USA). PCR-purified products were cloned into the pGEM-T Easy vector (Promega, WI, USA), and sequenced by Macrogen (Korea).

Primers and restriction enzymes were supplied by Invitrogen (CA, USA) and New England Biolabs (MA, USA), respectively. Taq polymerase and Elongase were purchased from Promega and Invitrogen, respectively.

Amplification of a DNA Fragment Encoding a Xylanase

Two primers (SEQ ID NOS: 3, 4) were designed. The sense primer SEQ ID NO: 3 and the antisense primer SEQ ID NO: 4 were able to amplify a central region of the gene encoding the *Psychrobacter*-derived cold adapted family GH10 xylanase-like protein (SEQ ID NO: 5). The amplified genes were cloned in a pGEM-T system (Promega) and selected clones were automatically sequenced. To complete the rest of the xylanase encoding gene, a new method of genome walking was implemented (Acevedo et al., 2008, "Cloning of complete genes for novel hydrolytic enzymes from Antarctic sea water bacteria by use of an improved genome walking technique," *J. Biotechnol.*, 133, 277-86)

Genome Walking Method

1) Construction of Oligo-Cassette:

A double-stranded oligo-cassette AdaptT adapter was constructed by annealing of the two unphosphorylated primers AdaptF and AdaptR (SEQ ID NOS: 6, 7) Annealing was performed by heating the primers (10 μM) in a boiling water bath, and then slowly cooling to room temperature. This cassette has a 3' overhanging thymidine.

2) Construction of Oligo-Cassette Libraries:

For construction of DNA fragments linked to the oligo-cassette AdaptT, 1 μg of genomic DNA was digested with 10 activity units of a restriction enzyme (HindIII, XbaI, EcoRV, EcoRI, Sau3AI, PvuII) and 2 μl of 10× enzyme reaction buffer in 20 μl reaction volume. To complete the 3' recessive end of the fragments and to add a 3' overhanging adenine, 500 ng of the digested and purified DNA were incubated with 5 activity units of Taq DNA polymerase, 1 μl of 10 mM dNTPs mix (dATP, dTTP, dGTP and dCTP) and 5 μl of 10× thermophilic DNA polymerase buffer in 50 μl total volume, at 70° C. for 45 min. 7 μl of this mixture was incubated with 15 μmoles of AdaptT oligo-cassette, 1 unit T4 DNA ligase (Invitrogen) and 2 μl of 5× ligase buffer, in a total volume of 10 μl. The ligation reaction was incubated at 16° C. overnight.

3) First Round of PCR

The amplification reaction was performed in a volume of 50 μl with 1× Elongase mix buffer, 1.9 mM $MgCl_2$, 0.2 mM dNTPs, 0.5 μM first specific primer (designed from the known sequence of the target gene (SEQ ID NO: 5); it should be a forward primer to amplify the 3' end (SEQ ID NO: 9) or a reverse primer to amplify the 5' end (SEQ ID NO: 10)), 5 μl of the ligated DNA diluted 10 fold and 1 μl of Elongase. The thermal cycling conditions were: 1 cycle at 94° C. for 1 min., 20 cycles at 94° C. for 32 sec., 1 cycle at 68° C. for 5 min., and 1 final additional cycle at 70° C. for 7 min. Reactions were carried out in an Eppendorf Master Cycler Gradient (HA, GE). The PCR product was diluted 10 fold and 3 μl were used as a DNA template for second PCR.

4) Second Round of PCR

The second amplification reaction was performed in a total volume of 50 μl of 1× Elongase mix buffer, where the final concentrations were: 1.9 mM $MgCl_2$, 0.2 mM dNTPs, 0.5 μM second specific primer (designed from the known sequence of the target gene (SEQ ID NO: 5); it should be a forward primer to amplify the 3' end (SEQ ID NO: 11) or a reverse primer to amplify the 5' end (SEQ ID NO: 12)), 0.2 μM oligo-cassette-specific primer AdaptF2 (SEQ ID NO: 8), 3 μl of the diluted product from the first PCR and 1 μl of Elongase. The thermal cycling conditions were: 1 cycle at 94° C. for 1 min., 35 cycles at 94° C. for 32 sec., 1 cycle at 68° C. for 5 min., and 1 final additional cycle at 70° C. for 7 min.

5) Construction of the Complete Nucleic Acid Sequence:

The amplifications of the second PCR (5' and 3') were cloned in a pGEM-T system (Promega) and selected clones were automatically sequenced. By overlapping the sequences previously amplified it was possible to obtain the whole nucleotide sequence of the subtilisin-like encoding gene. In order to be sure about the correct sequence of the gene, two primers were designed from the ends of the gene and another amplification was performed using a high-fidelity DNA polymerase. The amplifications were cloned in a pGEM-T system (Promega) and selected clones were automatically sequenced.

Example 2

Construction of Expression Vector and Expression of the Protein of the Invention With the sequences obtained with the new genome walking method, two primers (SEQ ID NOS: 13, 14) were designed and a final PCR was carried out. In addition, cloning and sequencing of the complete gene which encodes the purified protein of the present invention were completed. Eight clones were analyzed, representing the same gene (amino acid residues 61-2220 of SEQ ID NO: 1). The *Psychrobacter*-derived cold adapted family GH10 xylanase-like protein was expressed in *E. coli* using the NcoI and XhoI sites of a pET22b vector provided by Novagen. The pET vector places the recombinant protein under the control of bacteriophage T7 transcription and translation signals. Once established in a non-expression host, *E. coli* DH5α, the plasmid was then transferred to an expression host, *E. coli* BL21 (DE3) pLYS S having a chromosomal copy of the T7 polymerase gene under lacUV5 control. Expression was induced by the addition of IPTG.

Example 3

Characterization of the Genomic Sequence Encoding a Family GH10A Xylanase

The genomic fragment encodes a polypeptide of 740 amino acids. The % G+C content of the gene is 42%. Using the LipoP 1.0 Server (Juncker et al., 2003, "Prediction of lipoprotein signal peptides in Gram-negative bacteria," Protein Sci., 12: 1652-62), a signal peptide of 20 residues was predicted. The predicted mature protein contains 720 amino acids with a molecular mass of 80 kDa. Two carbohydrate binding domains were identified using the National Center for Biotechnology Information server (http://www.ncbi.nlm.nih.gov/BLAST/), which comprises 474 bp from nucleotide 157 to nucleotide 630 encoding 158 amino acids (amino acids 53 to 210 of SEQ ID NO: 2) and 459 bp from nucleotide 1775 to nucleotide 2223 encoding 152 amino acids (amino acids 589 to 740 of SEQ ID NO: 2). A catalytic domain was identified using the National Center for Biotechnology Information server (http://www.ncbi.nlm.nih.gov/BLAST/), which comprises 1029 bp from nucleotide 700 to nucleotide 1728 encoding 343 amino acids (amino acids 234 to 576 of SEQ ID NO: 2)

Example 4

Expression of the Psychrobacter-Derived Cold Adapted Family GH10 Xylanase Gene in Escherichia coli BL21

Electrocompetent *Escherichia coli* BL21 cells were prepared according to Sambrook, J., Fristsch, E. and Maniatis, T., 2001, "Molecular cloning: a laboratory manual," New York: CSHL Press, Cold Spring Harbor. p. A8.9-A8.10. Recombinant plasmid was mixed with electrocompetent cells, and electroporated. The transformation yielded about 200 transformants. Twenty four transformants were transferred to agar plates with an overlay of soluble xylan agar and incubated at 37° C. overnight. Twenty one transformants formed halos around the colonies when stained with Congo red, indicating expression of xylanase activity.

For the recombinant expression of the xylanase, one of the positive transformants was grown overnight with shaking (200 rpm) at 37° C. in 250 mL of TB broth supplemented with ampicillin 0.01%. Expression was performed according to the supplier's instructions. When the optical density became 0.5 at 600 nm, isopropylthiogalactoside (IPTG) was added to a final concentration of 0.3 mM, and the growth temperature was lowered to 18° C. After 24 hours of cultivation, cells were harvested by centrifugation and culture supernatant was removed and assayed for xylanase activity.

Culture supernatants prepared as described above were assayed for xylanase activity as described below. Briefly, 50 µl of assay buffer (soluble birchwood in buffer tris/HC150 mM, $CaCl_2$, pH 8) were mixed with 50 µl of supernatant samples. Xylanase activities of the transformants were determined measuring the absorbance at 550 nm as was described in the DNS method (G. L. Miller, 1959, "Use of dinitrosalicylic acid reagent for determination of reducing sugars," *Anal. Chem.*, 3, 426-428). All of the transformants were found to express xylanase activity. SDS-PAGE (BioRad Criterion 10-12% SDS-PAGE) analysis of the supernatants showed a major band at approximately 80 kDa.

Sequences

The nucleic acid sequences described herein, and consequently the protein sequences derived therefrom, have been carefully sequenced. However, those of ordinary skill will recognize that nucleic acid sequencing technology can be susceptible to some inadvertent error. Those of ordinary skill in the relevant art are capable of validating or correcting these sequences based on the ample description herein of methods of isolating the nucleic acid sequences in question and such modifications that are made readily available by the present disclosure are encompassed by the present invention. Furthermore, those sequences reported herein are believed to define functional biological macromolecules within the invention whether or not later clarifying studies identify sequencing errors.

The foregoing discussion of the various embodiments of the invention has been presented for the purpose of illustration and description only. The scope of the invention is to be determined by the claims appended hereto.

What is claimed is:

1. An isolated polypeptide encoded by a cDNA with a nucleotide sequence comprising nucleotides identical to nucleotides at positions 1072-1134 and 1426-1488 of SEQ ID NO: 1 or a degenerate variant thereof having xylanase activity, with proviso that the cDNA does not have a sequence identical to SEQ ID NO: 1.

2. The polypeptide of claim 1, comprising an amino acid sequence selected from:
   a) amino acid residues 20-740 of SEQ ID NO: 2;
   b) amino acid residues 20-576 of SEQ ID NO: 2;
   c) amino acid residues 53-576 of SEQ ID NO: 2;
   d) amino acid residues 53-740 of SEQ ID NO: 2;
   f) amino acid residues 234-576 of SEQ ID NO: 2; and
   g) amino acid residues 234-740 of SEQ ID NO: 2.

3. A composition or product comprising one or more polypeptides as defined in claim 1.

4. The polypeptide of claim 1, having an amino acid sequence which has at least about 90% sequence identity with one of the following amino acid sequences:
   a) amino acid residues 20-740 of SEQ ID NO: 2;
   b) amino acid residues 20-576 of SEQ ID NO: 2;
   c) amino acid residues 53-576 of SEQ ID NO: 2;
   d) amino acid residues 53-740 of SEQ ID NO: 2;
   f) amino acid residues 234-576 of SEQ ID NO: 2; and
   g) amino acid residues 234-740 of SEQ ID NO: 2.

5. The polypeptide of claim 1, having an amino acid sequence which has at least about 95% sequence identity with one of the following amino acid sequences
   a) amino acid residues 20-740 of SEQ ID NO: 2;
   b) amino acid residues 20-576 of SEQ ID NO: 2;
   c) amino acid residues 53-576 of SEQ ID NO: 2;
   d) amino acid residues 53-740 of SEQ ID NO: 2;
   f) amino acid residues 234-576 of SEQ ID NO: 2; and
   g) amino acid residues 234-740 of SEQ ID NO: 2.

6. The polypeptide of claim 1, having an amino acid sequence which has at least about 96% sequence identity with one of the following amino acid sequences:
   a) amino acid residues 20-740 of SEQ ID NO: 2;
   b) amino acid residues 20-576 of SEQ ID NO: 2;
   c) amino acid residues 53-576 of SEQ ID NO: 2;
   d) amino acid residues 53-740 of SEQ ID NO: 2;
   f) amino acid residues 234-576 of SEQ ID NO: 2; and
   g) amino acid residues 234-740 of SEQ ID NO: 2.

7. The polypeptide of claim 1, having an amino acid sequence which has at least about 97% sequence identity with one of the following amino acid sequences:
   a) amino acid residues 20-740 of SEQ ID NO: 2;
   b) amino acid residues 20-576 of SEQ ID NO: 2;
   c) amino acid residues 53-576 of SEQ ID NO: 2;
   d) amino acid residues 53-740 of SEQ ID NO: 2;
   f) amino acid residues 234-576 of SEQ ID NO: 2; and
   g) amino acid residues 234-740 of SEQ ID NO: 2.

8. The polypeptide of claim 1, having an amino acid sequence which has at least about 98% sequence identity with one of the following amino acid sequences:
   a) amino acid residues 20-740 of SEQ ID NO: 2;
   b) amino acid residues 20-576 of SEQ ID NO: 2;
   c) amino acid residues 53-576 of SEQ ID NO: 2;
   d) amino acid residues 53-740 of SEQ ID NO: 2;
   f) amino acid residues 234-576 of SEQ ID NO: 2; and
   g) amino acid residues 234-740 of SEQ ID NO: 2.

9. The polypeptide of claim 1, having an amino acid sequence which has at least about 99% sequence identity with one of the following amino acid sequences:
   a) amino acid residues 20-740 of SEQ ID NO: 2;
   b) amino acid residues 20-576 of SEQ ID NO: 2;
   c) amino acid residues 53-576 of SEQ ID NO: 2;
   d) amino acid residues 53-740 of SEQ ID NO: 2;
   f) amino acid residues 234-576 of SEQ ID NO: 2; and
   g) amino acid residues 234-740 of SEQ ID NO: 2.

* * * * *

UNITED STATES PATENT AND TRADEMARK OFFICE
CERTIFICATE OF CORRECTION

PATENT NO. : 8,679,814 B2  Page 1 of 1
APPLICATION NO. : 13/148227
DATED : March 25, 2014
INVENTOR(S) : Asenjo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 68 days.

Signed and Sealed this
Twenty-ninth Day of September, 2015

Michelle K. Lee
*Director of the United States Patent and Trademark Office*